United States Patent
Inochkin et al.

(10) Patent No.: US 7,531,967 B2
(45) Date of Patent: May 12, 2009

(54) FLASHLAMP DRIVE CIRCUIT

(75) Inventors: Mikhail Inochkin, St. Petersburg (RU);
Vycheslav V. Togatov, St. Petersburg (RU); Peter O. Gnatyuk, St. Petersburg (RU)

(73) Assignee: Palomar Medical Technologies, Inc., Burlington, MA (US)

( * ) Notice: Subject to any disclaimer, the term of this patent is extended or adjusted under 35 U.S.C. 154(b) by 0 days.

(21) Appl. No.: 11/860,149

(22) Filed: Sep. 24, 2007

(65) Prior Publication Data
US 2008/0033413 A1    Feb. 7, 2008

Related U.S. Application Data

(63) Continuation of application No. 10/600,167, filed on Jun. 20, 2003, now Pat. No. 6,888,319, which is a continuation-in-part of application No. 10/267,610, filed on Oct. 9, 2002, now abandoned, and a continuation of application No. 09/797,501, filed on Mar. 1, 2001, now abandoned.

(51) Int. Cl.
   *H05B 41/16*    (2006.01)
(52) U.S. Cl. ................ 315/274; 315/279; 315/344; 315/347; 315/355
(58) Field of Classification Search ............ 315/347, 315/348, 349, 354, 355, 356, 344
See application file for complete search history.

(56) References Cited

U.S. PATENT DOCUMENTS

| | | | |
|---|---|---|---|
| 1,706,161 | A | 3/1929 | Hollnagel |
| 2,472,385 | A | 6/1949 | Rollman |
| 3,327,712 | A | 6/1967 | Kaufman et al. |
| 3,486,070 | A | 12/1969 | Engel |

(Continued)

FOREIGN PATENT DOCUMENTS

AT    400305    4/1995

(Continued)

OTHER PUBLICATIONS

Altea Therapeutics—Medicines Made Better (single page website print-out).

(Continued)

*Primary Examiner*—Tuyet Vo
(74) *Attorney, Agent, or Firm*—Thomas J. Engellenner; Reza Mollaaghababa; Nutter McClennen & Fish LLP

(57) ABSTRACT

The invention provides a power supply or drive circuit for a pulsed flashlamp which utilizes a two-core component having common windings as both an inductor for arc mode drive and for breakdown triggering of the lamp. Discharge of a capacitor through the inductor and lamp is controlled by a high-speed semiconductor switch which is turned on and off by a suitable control, current flowing from the inductor through a one-way path including the lamp when the switch is off. The control maintains the ratio of the power variation through the lamp to the average power through the lamp substantially constant. The controls may also be utilized to control output pulse shape. Novel protective features are also provided for circuit components during turn on periods for the switch.

8 Claims, 5 Drawing Sheets

U.S. PATENT DOCUMENTS

| | | |
|---|---|---|
| 3,527,932 A | 9/1970 | Thomas |
| 3,538,919 A | 11/1970 | Meyer |
| 3,597,652 A | 8/1971 | Gates, Jr. |
| 3,622,743 A | 11/1971 | Muncheryan |
| 3,653,778 A | 4/1972 | Freiling |
| 3,693,623 A | 9/1972 | Harte et al. |
| 3,818,914 A | 6/1974 | Bender |
| 3,834,391 A | 9/1974 | Block |
| 3,846,811 A | 11/1974 | Nakamura et al. |
| 3,857,015 A | 12/1974 | Clark et al. |
| 3,890,537 A | 6/1975 | Park et al. |
| 3,900,034 A | 8/1975 | Katz |
| 3,913,002 A | 10/1975 | Steigerwald et al. |
| 4,233,493 A | 11/1980 | Nath |
| 4,273,109 A | 6/1981 | Enderby |
| 4,275,335 A | 6/1981 | Ishida |
| 4,316,467 A | 2/1982 | Muckerheide |
| 4,388,924 A | 6/1983 | Weissman et al. |
| 4,456,872 A | 6/1984 | Froeschle |
| 4,461,294 A | 7/1984 | Baron |
| 4,524,289 A | 6/1985 | Hammond et al. |
| 4,539,987 A | 9/1985 | Nath et al. |
| 4,561,440 A | 12/1985 | Kubo et al. |
| 4,591,762 A | 5/1986 | Nakamura |
| 4,601,753 A | 7/1986 | Soileau et al. |
| 4,608,978 A | 9/1986 | Rohr |
| 4,617,926 A | 10/1986 | Sutton |
| 4,623,929 A | 11/1986 | Johnson et al. |
| 4,677,347 A | 6/1987 | Nakamura |
| 4,695,697 A | 9/1987 | Kosa |
| 4,718,416 A | 1/1988 | Nanaumi |
| 4,733,660 A | 3/1988 | Itzkan |
| 4,745,909 A | 5/1988 | Pelton et al. |
| 4,747,660 A | 5/1988 | Nishioka et al. |
| 4,749,913 A | 6/1988 | Stuermer et al. |
| 4,819,669 A | 4/1989 | Politzer |
| 4,832,024 A | 5/1989 | Boussignac et al. |
| 4,860,172 A | 8/1989 | Schlager et al. |
| 4,860,744 A | 8/1989 | Johnson et al. |
| 4,884,560 A | 12/1989 | Kuracina |
| 4,905,690 A | 3/1990 | Ohshiro et al. |
| 4,917,084 A | 4/1990 | Sinofsky |
| 4,926,227 A | 5/1990 | Jensen |
| 4,928,038 A | 5/1990 | Nerone |
| 4,930,504 A | 6/1990 | Diamantopoulos et al. |
| 4,945,239 A | 7/1990 | Wist et al. |
| 5,000,752 A | 3/1991 | Hoskin et al. |
| 5,057,104 A | 10/1991 | Chess |
| 5,059,192 A | 10/1991 | Zaias |
| 5,065,515 A | 11/1991 | Iderosa |
| 5,066,293 A | 11/1991 | Furumoto |
| 5,071,417 A | 12/1991 | Sinofsky |
| 5,108,388 A | 4/1992 | Trokel |
| 5,127,395 A | 7/1992 | Bontemps |
| 5,137,530 A | 8/1992 | Sand |
| 5,140,984 A | 8/1992 | Dew et al. |
| 5,178,617 A | 1/1993 | Kuizenga et al. |
| 5,182,557 A | 1/1993 | Lang |
| 5,182,857 A | 2/1993 | Simon |
| 5,196,004 A | 3/1993 | Sinofsky |
| 5,207,671 A | 5/1993 | Franken et al. |
| 5,225,926 A | 7/1993 | Cuomo et al. |
| 5,226,907 A | 7/1993 | Tankovich |
| 5,267,399 A | 12/1993 | Johnston |
| 5,282,797 A | 2/1994 | Chess |
| 5,287,372 A | 2/1994 | Ortiz |
| 5,287,380 A | 2/1994 | Hsia |
| 5,300,097 A | 4/1994 | Lerner et al. |
| 5,304,170 A | 4/1994 | Green |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,342,358 A | 8/1994 | Daikuzono et al. |
| 5,344,418 A | 9/1994 | Ghaffari |
| 5,344,434 A | 9/1994 | Talmore |
| 5,348,551 A | 9/1994 | Spears et al. |
| 5,350,376 A | 9/1994 | Brown |
| 5,358,503 A | 10/1994 | Bertwell et al. |
| 5,380,317 A | 1/1995 | Everett et al. |
| 5,403,306 A | 4/1995 | Edwards et al. |
| 5,405,368 A | 4/1995 | Eckhouse |
| 5,415,654 A | 5/1995 | Daikuzono |
| 5,425,728 A | 6/1995 | Tankovich |
| 5,458,140 A | 10/1995 | Eppstein et al. |
| 5,474,549 A | 12/1995 | Ortiz et al. |
| 5,486,172 A | 1/1996 | Chess |
| 5,505,726 A | 4/1996 | Meserol |
| 5,505,727 A | 4/1996 | Keller |
| 5,519,534 A | 5/1996 | Smith |
| 5,522,813 A | 6/1996 | Trelles |
| 5,531,739 A | 7/1996 | Trelles |
| 5,531,740 A | 7/1996 | Black |
| 5,549,660 A | 8/1996 | Mendes et al. |
| 5,558,667 A | 9/1996 | Yarborough et al. |
| 5,578,866 A | 11/1996 | DePoorter et al. |
| 5,595,568 A | 1/1997 | Anderson et al. |
| 5,616,140 A | 4/1997 | Prescott |
| 5,620,478 A | 4/1997 | Eckhouse |
| 5,626,631 A | 5/1997 | Eckhouse |
| 5,630,811 A | 5/1997 | Miller |
| 5,649,972 A | 7/1997 | Hochstein |
| 5,652,481 A | 7/1997 | Johnson et al. |
| 5,653,706 A | 8/1997 | Zavislan et al. |
| 5,655,547 A | 8/1997 | Karni |
| 5,658,148 A | 8/1997 | Neuberger et al. |
| 5,658,323 A | 8/1997 | Miller |
| 5,660,836 A | 8/1997 | Knowlton |
| 5,662,643 A | 9/1997 | Kung et al. |
| 5,662,644 A | 9/1997 | Swor |
| 5,683,380 A | 11/1997 | Eckhouse et al. |
| 5,698,866 A | 12/1997 | Doiron et al. |
| 5,707,403 A | 1/1998 | Grove et al. |
| 5,720,772 A | 2/1998 | Eckhouse |
| 5,722,397 A | 3/1998 | Eppstein |
| 5,735,844 A | 4/1998 | Anderson et al. |
| 5,735,884 A | 4/1998 | Thompson et al. |
| 5,742,392 A | 4/1998 | Anderson et al. |
| 5,743,901 A | 4/1998 | Grove et al. |
| 5,746,735 A | 5/1998 | Furumoto et al. |
| 5,755,751 A | 5/1998 | Eckhouse |
| 5,759,200 A | 6/1998 | Azar |
| 5,769,076 A | 6/1998 | Mackawa et al. |
| 5,782,249 A | 7/1998 | Weber et al. |
| 5,810,801 A | 9/1998 | Anderson et al. |
| 5,814,008 A | 9/1998 | Chen et al. |
| 5,814,040 A | 9/1998 | Nelson et al. |
| 5,814,041 A | 9/1998 | Anderson et al. |
| 5,817,089 A | 10/1998 | Tankovich et al. |
| 5,820,625 A | 10/1998 | Izawa et al. |
| 5,820,626 A | 10/1998 | Baumgardner |
| 5,824,023 A | 10/1998 | Anderson |
| 5,827,264 A | 10/1998 | Hohla |
| 5,828,803 A | 10/1998 | Eckhouse |
| 5,830,208 A | 11/1998 | Muller |
| 5,836,877 A | 11/1998 | Zavislan |
| 5,836,999 A | 11/1998 | Eckhouse et al. |
| 5,840,048 A | 11/1998 | Cheng |
| 5,849,029 A | 12/1998 | Eckhouse et al. |
| 5,851,181 A | 12/1998 | Talmor |
| 5,853,407 A | 12/1998 | Miller |
| 5,860,967 A | 1/1999 | Zavislan et al. |
| 5,868,731 A | 2/1999 | Budnik et al. |
| 5,871,480 A | 2/1999 | Tankovich |

| | | |
|---|---|---|
| 5,883,471 A | 3/1999 | Rodman et al. |
| 5,885,211 A | 3/1999 | Eppstein et al. |
| 5,885,273 A | 3/1999 | Eckhouse et al. |
| 5,885,274 A | 3/1999 | Fullmer et al. |
| 5,891,063 A | 4/1999 | Vigil |
| 5,893,828 A | 4/1999 | Uram |
| 5,913,883 A | 6/1999 | Alexander et al. |
| 5,916,211 A | 6/1999 | Quon et al. |
| 5,920,374 A | 7/1999 | Vaphiades et al. |
| 5,944,748 A | 8/1999 | Mager et al. |
| 5,948,011 A | 9/1999 | Knowlton |
| 5,949,222 A | 9/1999 | Buono |
| 5,954,710 A | 9/1999 | Paolini et al. |
| 5,955,490 A | 9/1999 | Kennedy et al. |
| 5,964,749 A | 10/1999 | Eckhouse et al. |
| 5,968,033 A | 10/1999 | Fuller |
| 5,968,034 A | 10/1999 | Fullmer et al. |
| 5,977,723 A | 11/1999 | Yoon |
| 5,984,915 A | 11/1999 | Loeb et al. |
| 6,015,404 A | 1/2000 | Altshuler et al. |
| 6,022,316 A | 2/2000 | Epstein et al. |
| 6,026,828 A | 2/2000 | Altshuler |
| 6,027,495 A | 2/2000 | Miller |
| 6,030,399 A | 2/2000 | Ignotz et al. |
| 6,032,071 A | 2/2000 | Binder |
| RE36,634 E | 3/2000 | Ghaffari |
| 6,036,684 A | 3/2000 | Tankovich et al. |
| 6,050,990 A | 4/2000 | Tankovich et al. |
| D424,197 S | 5/2000 | Sydlowski et al. |
| 6,056,738 A | 5/2000 | Marchitto et al. |
| 6,059,820 A | 5/2000 | Baronov |
| 6,074,382 A | 6/2000 | Asah et al. |
| 6,080,146 A | 6/2000 | Altshuler et al. |
| 6,080,147 A | 6/2000 | Tobinick |
| 6,086,580 A | 7/2000 | Mordon et al. |
| 6,094,767 A | 8/2000 | Iimura |
| 6,096,029 A | 8/2000 | O'Donnell, Jr. |
| 6,096,209 A | 8/2000 | O'Brien et al. |
| 6,104,959 A | 8/2000 | Spertell |
| 6,117,129 A | 9/2000 | Mukai |
| 6,120,497 A | 9/2000 | Anderson |
| 6,142,650 A | 11/2000 | Brown et al. |
| 6,142,939 A | 11/2000 | Eppstein et al. |
| 6,149,644 A | 11/2000 | Xie |
| 6,162,055 A | 12/2000 | Montgomery et al. |
| 6,162,211 A | 12/2000 | Tankovich et al. |
| 6,162,212 A | 12/2000 | Kreindel et al. |
| 6,173,202 B1 | 1/2001 | Eppstein |
| 6,174,325 B1 | 1/2001 | Eckhouse |
| 6,176,854 B1 | 1/2001 | Cone |
| 6,183,434 B1 | 2/2001 | Eppstein |
| 6,183,500 B1 | 2/2001 | Kohler |
| 6,183,773 B1 | 2/2001 | Anderson |
| 6,187,001 B1 | 2/2001 | Azar et al. |
| 6,197,020 B1 | 3/2001 | O'Donnell |
| 6,200,309 B1 | 3/2001 | Rice et al. |
| 6,210,425 B1 | 4/2001 | Chen |
| 6,214,034 B1 | 4/2001 | Azar |
| 6,228,075 B1 | 5/2001 | Furumoto |
| 6,229,831 B1 | 5/2001 | Nightingale et al. |
| 6,235,016 B1 | 5/2001 | Stewart |
| 6,236,891 B1 | 5/2001 | Ingel et al. |
| 6,245,093 B1 | 6/2001 | Li et al. |
| 6,263,233 B1 | 7/2001 | Zavislan et al. |
| 6,264,649 B1 | 7/2001 | Whitcroft et al. |
| 6,267,780 B1 | 7/2001 | Streeter |
| 6,273,884 B1 | 8/2001 | Altshuler et al. |
| 6,273,885 B1 | 8/2001 | Koop et al. |
| 6,280,438 B1 | 8/2001 | Eckhouse et al. |
| 6,283,956 B1 | 9/2001 | McDaniel |
| 6,290,713 B1 | 9/2001 | Russell |
| 6,306,130 B1 | 10/2001 | Anderson et al. |
| 6,306,160 B1 | 10/2001 | Nidetzky |
| 6,319,274 B1 | 11/2001 | Shadduck |
| 6,331,111 B1 | 12/2001 | Cao |
| 6,340,495 B1 | 1/2002 | Sumian et al. |
| 6,343,933 B1 | 2/2002 | Montgomery et al. |
| 6,350,276 B1 | 2/2002 | Knowlton |
| 6,354,370 B1 | 3/2002 | Miller et al. |
| 6,358,272 B1 | 3/2002 | Wilden |
| 6,383,176 B1 | 5/2002 | Connors et al. |
| 6,383,177 B1 | 5/2002 | Balle-Petersen et al. |
| 6,387,089 B1 | 5/2002 | Kreindel et al. |
| 6,402,739 B1 | 6/2002 | Neev |
| 6,406,474 B1 | 6/2002 | Neuberger et al. |
| 6,424,852 B1 | 7/2002 | Zavislan |
| 6,425,912 B1 | 7/2002 | Knowlton |
| 6,436,094 B1 | 8/2002 | Reuter |
| 6,461,296 B1 | 10/2002 | Desai |
| 6,471,712 B2 | 10/2002 | Burres |
| 6,471,716 B1 | 10/2002 | Pecukonis |
| 6,475,211 B2 | 11/2002 | Chess et al. |
| 6,494,900 B1 | 12/2002 | Salansky et al. |
| 6,508,785 B1 | 1/2003 | Eppstein |
| 6,508,813 B1 | 1/2003 | Altshuler |
| 6,511,475 B1 | 1/2003 | Altshuler et al. |
| 6,514,243 B1 | 2/2003 | Eckhouse et al. |
| 6,517,532 B1 | 2/2003 | Altshuler et al. |
| 6,530,915 B1 | 3/2003 | Eppstein et al. |
| 6,537,270 B1 | 3/2003 | Elbrecht et al. |
| 6,547,780 B1 | 4/2003 | Sinofsky |
| 6,558,372 B1 | 5/2003 | Altshuler |
| 6,569,155 B1 | 5/2003 | Connors et al. |
| 6,572,637 B1 | 6/2003 | Yamazaki et al. |
| 6,602,245 B1 | 8/2003 | Thiberg |
| 6,605,080 B1 | 8/2003 | Altshuler et al. |
| 6,629,971 B2 | 10/2003 | McDaniel |
| 6,629,989 B2 | 10/2003 | Akita |
| 6,632,219 B1 | 10/2003 | Baranov et al. |
| 6,635,075 B2 | 10/2003 | Li et al. |
| 6,641,578 B2 | 11/2003 | Mukai |
| 6,641,600 B1 | 11/2003 | Kohler |
| 6,648,904 B2 | 11/2003 | Altshuler et al. |
| 6,653,618 B2 | 11/2003 | Zenzie |
| 6,659,999 B1 | 12/2003 | Anderson et al. |
| 6,660,000 B2 | 12/2003 | Neuberger et al. |
| 6,663,620 B2 | 12/2003 | Altshuler et al. |
| 6,663,658 B1 | 12/2003 | Kollias et al. |
| 6,663,659 B2 | 12/2003 | McDaniel |
| 6,676,654 B1 | 1/2004 | Balle-Petersen et al. |
| 6,679,837 B2 | 1/2004 | Daikuzono |
| 6,685,699 B1 | 2/2004 | Eppstein et al. |
| 6,689,124 B2 | 2/2004 | Thiberg |
| 6,706,035 B2 | 3/2004 | Cense et al. |
| 6,709,269 B1 | 3/2004 | Altshuler |
| 6,709,446 B2 | 3/2004 | Lundahl et al. |
| 6,723,090 B2 | 4/2004 | Altshuler et al. |
| 6,743,222 B2 | 6/2004 | Durkin et al. |
| 6,770,069 B1 | 8/2004 | Hobart et al. |
| 6,790,205 B1 | 9/2004 | Yamazaki et al. |
| 6,801,595 B2 | 10/2004 | Grodzins et al. |
| 6,808,532 B2 | 10/2004 | Andersen et al. |
| RE38,670 E | 12/2004 | Asah et al. |
| 6,862,771 B1 | 3/2005 | Muller |
| 6,878,144 B2 | 4/2005 | Altshuler et al. |
| 6,881,212 B1 | 4/2005 | Clement et al. |
| 6,887,260 B1 | 5/2005 | McDaniel |
| 6,888,319 B2 | 5/2005 | Inochkin et al. |
| 6,974,451 B2 | 12/2005 | Altshuler et al. |
| 6,976,985 B2 | 12/2005 | Altshuler et al. |
| 6,997,923 B2 | 2/2006 | Anderson et al. |
| 7,001,413 B2 | 2/2006 | Butler |
| 7,006,223 B2 | 2/2006 | Mullani |
| 7,029,469 B2 | 4/2006 | Vasily |
| 7,044,959 B2 | 5/2006 | Anderson et al. |
| 7,060,061 B2 | 6/2006 | Altshuler et al. |

| | | |
|---|---|---|
| 7,077,840 B2 | 7/2006 | Altshuler et al. |
| 7,097,656 B1 | 8/2006 | Akopov et al. |
| 7,274,155 B2 | 9/2007 | Inochkin et al. |
| 2001/0024777 A1 | 9/2001 | Azar et al. |
| 2001/0041886 A1 | 11/2001 | Durkin et al. |
| 2002/0005475 A1 | 1/2002 | Zenzie |
| 2002/0019624 A1 | 2/2002 | Clement |
| 2002/0026225 A1 | 2/2002 | Segal |
| 2002/0091377 A1 | 7/2002 | Anderson |
| 2002/0123745 A1 | 9/2002 | Svaasand et al. |
| 2002/0128635 A1 | 9/2002 | Altshuler et al. |
| 2002/0161357 A1 | 10/2002 | Anderson |
| 2002/0173780 A1 | 11/2002 | Altshuler et al. |
| 2003/0004499 A1 | 1/2003 | McDaniel |
| 2003/0018373 A1 | 1/2003 | Eckhardt et al. |
| 2003/0023235 A1 | 1/2003 | Cense et al. |
| 2003/0023283 A1 | 1/2003 | McDaniel |
| 2003/0032900 A1 | 2/2003 | Ella |
| 2003/0032950 A1 | 2/2003 | Altshuler et al. |
| 2003/0036680 A1 | 2/2003 | Black |
| 2003/0055414 A1 | 3/2003 | Altshuler et al. |
| 2003/0057875 A1 | 3/2003 | Inochkin et al. |
| 2003/0065314 A1 | 4/2003 | Altshuler et al. |
| 2003/0100936 A1 | 5/2003 | Altshuler et al. |
| 2003/0109787 A1 | 6/2003 | Black |
| 2003/0109860 A1 | 6/2003 | Black |
| 2003/0129154 A1 | 7/2003 | McDaniel |
| 2003/0187486 A1 | 10/2003 | Savage et al. |
| 2003/0195494 A1 | 10/2003 | Altshuler et al. |
| 2003/0199859 A1 | 10/2003 | Altshuler et al. |
| 2003/0216795 A1 | 11/2003 | Harth et al. |
| 2003/0232303 A1 | 12/2003 | Black |
| 2004/0006332 A1 | 1/2004 | Black |
| 2004/0010298 A1 | 1/2004 | Altshuler et al. |
| 2004/0015156 A1 | 1/2004 | Vasily |
| 2004/0024388 A1 | 2/2004 | Altshuler |
| 2004/0030326 A1 | 2/2004 | Altshuler et al. |
| 2004/0034319 A1 | 2/2004 | Anderson et al. |
| 2004/0034341 A1 | 2/2004 | Altshuler et al. |
| 2004/0073079 A1 | 4/2004 | Altshuler et al. |
| 2004/0082940 A1 | 4/2004 | Black et al. |
| 2004/0085026 A1 | 5/2004 | Inochkin et al. |
| 2004/0093042 A1 | 5/2004 | Altshuler et al. |
| 2004/0133251 A1 | 7/2004 | Altshuler et al. |
| 2004/0143920 A1 | 7/2004 | Nanda |
| 2004/0147984 A1 | 7/2004 | Altshuler et al. |
| 2004/0162549 A1 | 8/2004 | Altshule et al. |
| 2004/0162596 A1 | 8/2004 | Altshuler et al. |
| 2004/0176754 A1 | 9/2004 | Island et al. |
| 2004/0191729 A1 | 9/2004 | Altshuler et al. |
| 2004/0193234 A1 | 9/2004 | Butler |
| 2004/0193235 A1 | 9/2004 | Altshuler et al. |
| 2004/0193236 A1 | 9/2004 | Altshuler et al. |
| 2004/0199227 A1 | 10/2004 | Altshuler et al. |
| 2004/0204745 A1 | 10/2004 | Altshuler et al. |
| 2004/0210276 A1 | 10/2004 | Altshuler et al. |
| 2004/0214132 A1 | 10/2004 | Altshuler |
| 2004/0225339 A1 | 11/2004 | Yaroslavsky et al. |
| 2004/0230258 A1 | 11/2004 | Altshuler et al. |
| 2005/0038418 A1 | 2/2005 | Altshuler et al. |
| 2005/0049582 A1 | 3/2005 | DeBenedictis et al. |
| 2005/0049658 A1 | 3/2005 | Connors et al. |
| 2005/0107849 A1 | 5/2005 | Altshuler et al. |
| 2005/0168158 A1 | 8/2005 | Inochkin et al. |
| 2005/0171517 A1 | 8/2005 | Altshuler et al. |
| 2005/0197681 A1 | 9/2005 | Barolet et al. |
| 2005/0215988 A1 | 9/2005 | Altshuler et al. |
| 2006/0004306 A1 | 1/2006 | Altshuler et al. |
| 2006/0004347 A1 | 1/2006 | Altshuler et al. |
| 2006/0009750 A1 | 1/2006 | Altshuler et al. |
| 2006/0020309 A1 | 1/2006 | Altshuler et al. |
| 2006/0058712 A1 | 3/2006 | Anderson et al. |
| 2006/0122668 A1 | 6/2006 | Anderson et al. |
| 2006/0149343 A1 | 7/2006 | Altshuler et al. |
| 2006/0161143 A1 | 7/2006 | Altshuler et al. |
| 2006/0194164 A1 | 8/2006 | Altshuler et al. |
| 2006/0206103 A1 | 9/2006 | Altshuler et al. |
| 2006/0253176 A1 | 11/2006 | Caruso et al. |
| 2006/0271028 A1 | 11/2006 | Altshuler et al. |
| 2006/0287646 A1 | 12/2006 | Altshuler et al. |
| 2007/0027440 A1 | 2/2007 | Altshuler et al. |
| 2007/0038206 A1 | 2/2007 | Altshuler et al. |
| 2007/0049910 A1 | 3/2007 | Altshuler et al. |
| 2007/0060819 A1 | 3/2007 | Altshuler et al. |
| 2007/0067006 A1 | 3/2007 | Altshuler et al. |
| 2007/0073308 A1 | 3/2007 | Anderson et al. |
| 2007/0078501 A1 | 4/2007 | Altshuler et al. |
| 2007/0194717 A1 | 8/2007 | Belikov et al. |
| 2007/0198004 A1 | 8/2007 | Atlshuler et al. |
| 2007/0213696 A1 | 9/2007 | Altshuler et al. |
| 2007/0213698 A1 | 9/2007 | Altshuler et al. |
| 2007/0213792 A1 | 9/2007 | Yaroslavsky et al. |
| 2007/0219604 A1 | 9/2007 | Yaroslavsky et al. |
| 2007/0219605 A1 | 9/2007 | Yaroslavsky et al. |

FOREIGN PATENT DOCUMENTS

| | | |
|---|---|---|
| AU | 1851583 | 3/1984 |
| DE | 3837248 | 5/1990 |
| DE | 9102407 | 7/1991 |
| EP | 0142671 | 5/1985 |
| EP | 0565331 | 10/1993 |
| EP | 0598984 | 6/1994 |
| EP | 0709941 | 5/1996 |
| EP | 0724894 | 8/1996 |
| EP | 0726083 | 8/1996 |
| EP | 0736308 | 10/1996 |
| EP | 0743029 | 11/1996 |
| EP | 0755698 | 1/1997 |
| EP | 0763371 | 3/1997 |
| EP | 0765673 | 4/1997 |
| EP | 0765674 | 4/1997 |
| EP | 0783904 | 7/1997 |
| EP | 0884066 | 12/1998 |
| EP | 0885629 | 12/1998 |
| EP | 1038505 | 9/2000 |
| EP | 1075854 | 2/2001 |
| EP | 1138349 | 10/2001 |
| EP | 1147785 | 10/2001 |
| EP | 1219258 | 7/2002 |
| EP | 1226787 | 7/2002 |
| EP | 1250893 | 10/2002 |
| EP | 1 457 234 A2 | 9/2004 |
| FR | 2199453 | 4/1974 |
| FR | 2591902 | 6/1987 |
| GB | 1546625 | 5/1979 |
| GB | 2044908 | 10/1980 |
| GB | 2123287 | 2/1984 |
| GB | 2356570 | 5/2001 |
| GB | 2360946 | 10/2001 |
| GB | 2368020 | 4/2002 |
| GB | 2390021 | 12/2003 |
| GB | 2397528 | 7/2004 |
| JP | 2001145520 | 5/2001 |
| JP | 2003192809 | 2/2005 |
| RU | 2082337/95105406 | 6/1997 |
| RU | 2089126/94012665 | 10/1997 |
| RU | 2089127/94040344 | 10/1997 |
| RU | 2096051/95012749 | 11/1997 |
| RU | 2122848/4954402 | 10/1998 |
| WO | WO 86/02783 | 5/1986 |
| WO | WO 88/04592 | 6/1988 |
| WO | WO 90/00420 | 1/1990 |
| WO | WO 91/13652 | 9/1991 |
| WO | WO 92/16338 | 1/1992 |
| WO | WO 92/19165 | 11/1992 |

| | | |
|---|---|---|
| WO | WO 93/05920 | 4/1993 |
| WO | WO 95/15725 | 6/1995 |
| WO | WO 95/32441 | 11/1995 |
| WO | WO 96/23447 | 8/1996 |
| WO | WO 96/25979 | 8/1996 |
| WO | WO 96/36396 | 11/1996 |
| WO | WO 96/41579 | 12/1996 |
| WO | WO 97/13458 | 4/1997 |
| WO | WO 97/13552 | 4/1997 |
| WO | WO 98/04317 | 2/1998 |
| WO | WO 98/05380 | 2/1998 |
| WO | WO 98/24507 | 6/1998 |
| WO | WO 98/51235 | 11/1998 |
| WO | WO 98/52481 | 11/1998 |
| WO | WO 98/58595 | 12/1998 |
| WO | WO 98/17666 | 4/1999 |
| WO | WO 99/17667 | 4/1999 |
| WO | WO 99/27997 | 6/1999 |
| WO | WO 99/29243 | 6/1999 |
| WO | WO 99/38569 | 8/1999 |
| WO | WO 99/46005 | 9/1999 |
| WO | WO 99/49937 | 10/1999 |
| WO | WO 00/02491 | 1/2000 |
| WO | WO 00/03257 | 1/2000 |
| WO | WO 00/32272 | 6/2000 |
| WO | WO 00/40266 | 7/2000 |
| WO | WO 00/43070 | 7/2000 |
| WO | WO 00/44294 | 8/2000 |
| WO | WO 00/54649 | 9/2000 |
| WO | WO 00/64537 | 11/2000 |
| WO | WO 00/71045 | 11/2000 |
| WO | WO 00/74583 | 12/2000 |
| WO | WO 00/74781 | 12/2000 |
| WO | WO 00/78242 | 12/2000 |
| WO | WO 01/03257 | 1/2001 |
| WO | WO 01/26573 | 4/2001 |
| WO | WO 01/34048 | 5/2001 |
| WO | WO 01/42671 | 6/2001 |
| WO | WO 01/54606 | 8/2001 |
| WO | WO 01/54770 | 8/2001 |
| WO | WO 01/78830 | 10/2001 |
| WO | WO 02/053050 | 7/2002 |
| WO | WO 02/069825 | 9/2002 |
| WO | WO 02/094116 | 11/2002 |
| WO | WO 2004/033040 | 4/2004 |
| WO | WO 2004/073537 | 9/2004 |
| WO | WO 2004/084752 | 10/2004 |
| WO | WO 2004/086947 A2 | 10/2004 |
| WO | WO 2005/007003 A1 | 1/2005 |
| WO | WO 2005/030317 | 4/2005 |
| WO | WO 2006/036968 A2 | 4/2006 |

OTHER PUBLICATIONS

G.B. Altshuler et al., "Acoustic response of hard dental tissues to pulsed laser action," SPIE, vol. 2080, Dental Application of Lasers, pp. 97-103, 1993.

G.B. Altshuler et al., "Extended theory of selective photothermolysis," Lasers in Surgery and Medicine, vol. 29, pp. 416-432, 2001.

R.L. Amy & R. Storb, "Selective mitochondrial damage by a ruby laser microbeam: An electron microscopic study," Science, vol. 15, pp. 756-758, Nov. 1965.

R.R. Anderson et al., "The optics of human skin," Journal of Investigative Dermatology, vol. 77, No. 1, pp. 13-19, 1981.

R.R. Anderson & J.A. Parrish, "Selective photothermolysis: Precise microsurgery by selective absorption of pulsed radiation," Science, vol. 220, pp. 524-527, Apr. 1983.

A.V. Belikov et al., "Identification of enamel and dentine under tooth laser treatment," SPIE vol. 2623, Progress in Biomedical Optics Europe Series, Proceedings of Medical Applications of Lasers III, pp. 109-116, Sep. 1995.

P. Bjerring et al., "Selective Non-Ablative Wrinkle Reduction by Laser," J Cutan Laser Ther, vol. 2, pp. 9-15, 2000.

Derma Chiller advertisement (2 pages) from Paradigm Trex.

Doukas et al., "Transdermal Drug Delivery With a Pressure Wave," Advanced Drug Delivery Reviews 56 (2004), pp. 559-579.

J.S. Dover et al., "Pigmented guinea pig skin irradiated with Q-switched ruby laser pulses," Arch Dermatol, vol. 125, pp. 43-49, Jan. 1989.

L.H. Finkelstein & L.M. Blatstein, "Epilation of hair-bearing urethral grafts using the neodymium:yag surgical laser," Journal of Urology, vol. 146, pp. 840-842, Sep. 1991.

E.J. Fiskerstrand et al., "High Removal With Long Pulsed Diode Lasers: A Comparison Between Two Systems With Different Pulse Structures," Lasers in Surgery and Medicine, vol. 32, pp. 399-404, 2003.

L. Goldman, Biomedical Aspects of the Laser, Springer-Verlag New York Inc., publishers Chapts. 1, 2, & 23, 1967.

L. Goldman, "Dermatologic manifestations of laser radiation," Proceedings of the First Annual Conference on Biologic Effects of Laser Radiation, Federation of the American Societies for Experimental Biology, Supp. No. 14, pp. S-92-S-93, Jan.-Feb. 1965.

L. Goldman, "Effects of new laser systems on the skin," Arch Dermatol., vol. 108, pp. 385-390, Sep. 1973.

L. Goldman, "Laser surgery for skin cancer," New York State Journal of Medicine, pp. 1897-1900, Oct. 1977.

L. Goldman, "Surgery by laser for malignant melanoma," J. Dermatol. Surg. Oncol., vol. 5, No. 2, pp. 141-144, Feb. 1979.

L. Goldman, "The skin," Arch Environ Health, vol. 18, pp. 434-436, Mar. 1969.

L. Goldman & D.F. Richfield, "The effect of repeated exposures to laser beams," Acta derm.-vernereol., vol. 44, pp. 264-268, 1964.

L. Goldman & R.J. Rockwell, "Laser action at the cellular level," JAMA, vol. 198, No. 6, pp. 641-644, Nov. 1966.

L. Goldman & R.G. Wilson, "Treatment of basal cell epithelioma by laser radiation," JAMA, vol. 189, No. 10, pp. 773-775.

L. Goldman et al., "The biomedical aspects of lasers," JAMA, vol. 188, No. 3, pp. 302-306, Apr. 1964.

L. Goldman et al., "Effect of the laser beam on the skin, Preliminary report" Journal of Investigative Dermatology, vol. 40, pp. 121-122, 1963.

L. Goldman et al., "Effect of the laser beam on the skin, III. Exposure of cytological preparations," Journal of Investigative Dermatology, vol. 42, pp. 247-251, 1964.

L. Goldman et al., "Impact of the laser on nevi and melanomas," Archives of Dermatology, vol. 90, pp. 71-75, Jul. 1964.

L. Goldman et al., "Laser treatment of tattoos, A preliminary survey of three year's clinical experience," JAMA, vol. 201, No. 11, pp. 841-844, Sep. 1967.

L. Goldman et al., "Long-term laser exposure of a senile freckle," ArchEnviron Health, vol. 22, pp. 401-403, Mar. 1971.

L. Goldman et al., "Pathology, Pathology of the effect of the laser beam on the skin," Nature, vol. 197, No. 4870, pp. 912-914, Mar. 1963.

L. Goldman et al., "Preliminary investigation of fat embolization from pulsed ruby laser impacts of bone," Nature, vol. 221, pp. 361-363, Jan. 1969.

L. Goldman et al., "Radiation from a Q-switched ruby laser, Effect of repeated impacts of power output of 10 megawatts on a tattoo of man," Journal of Investigative Dermatology, vol. 44, pp. 69-71, 1965.

L. Goldman et al., "Replica microscopy and scanning electron microscopy of laser impacts on the skin," Journal of Investigative Dermatology, vol. 52, No. 1, pp. 18-24, 1969.

M.C. Grossman et al., "Damage to hair follicles by normal-mode ruby laser pulses," Journal of he American Academy of Dermatology, vol. 35, No. 6, pp. 889-894, Dec. 1996.

M.C. Grossman et al., "Laser Targeted at Hair Follicles," Lasers Med Surg., Suppl. 7:221, 1995.

E. Klein et al., "Biological effects of laser radiation 1.," Northeast Electroncis Research and Engineering Meeting, NEREM Record, IEEE catalogue No. F-60, pp. 108-109, 1965.

J.G. Kuhns et al., "Laser injury in skin," Laboratory Investigation, vol. 17, No. 1, pp. 1-13, Jul. 1967.

J.G. Kuhns et al., "Biological effects of laser radiation II Effects of laser irradiation on the skin," NEREM Record, pp. 152-153, 1965.

D. Manstein et al., "Selective Photothermolysis of Lipid-Rich Tissue," American Society for Laser Medicine and Surgery Abstracts, No. 17, American Society for Laser Medicine and Surgery Twenty-First Annual Meeting, Apr. 20-22, 2001, p. 6.

R.J. Margolis et al., "Visible action spectrum for melanin-specific selective photothermolysis," Lasers in Surgery and Medicine, vol. 9, pp. 389-397, 1989.

Ohshiro et al., "The Ruby and Argon Lasers in the Treatment of the Naevi," Annals Academy of Medicine, Apr. 1983, vol. 12, No. 2, pp. 388-395.

J.A. Parrish, "Selective thermal effects with pulsed irradiation from lasers: From organ to organelle," Journal of Investigative Dermatology, vol. 80, No. 6 Supplement, pp. 75s-80s, 1983.

L. Polla et al., "Melanosomes are a primary target of Q-switched ruby laser irradiation in guinea pig skin," Journal of Investigative Dermatology, vol. 89, No. 3, pp. 281-286, Sep. 1987.

Riggle et al., "Laser Effects On Normal And Tumor Tissue," Laser Applications in Medicine and Biology, vol. 1, M.L. Wolbarsht, editor, Plenum Press, publishers, Chapter 3, pp. 35-65, 1971.

T. Shimbashi & T. Kojima, "Ruby laser treatment of pigmented skin lesions," Aesth. Plast. Surg., vol. 19, pp. 225-229, 1995.

Stratton, K., et al., "Biological Effects of Laser Radiation II: ESR Studies of Melanin Containing Tissues after Laser Irradiation," Northeast Electronics Research and Engineering Meeting—NEREM Record, IEEE Catalogue No. F-60, pp. 150-151, Nov. 1965.

Sumian, C.C. et al., "A Preliminary Clinical And Histopathological Study Of Laser Skin Resurfacing Using A Frequency-Doubled Nd:YAG Laser After Application of Chromofilm®," Journal of Cutaneous Laser Therapy, vol. 1, pp. 159-166, 1999.

Sumian, C.C. et al., "Laser Skin Resurfacing Using A Frequency Doubled Nd:YAG Laser After Topical Application Of An Exogenous Chromophore," Lasers in Surgery and Medicine, vol. 25, pp. 43-50, 1999.

C.R. Taylor et al., "Treatment of tattoos by Q-switched ruby laser," Arch. Dermatol. vol. 126, pp. 893-899, Jul. 1990.

V.V. Tuchin, "Laser light scattering in biomedical diagnostics and therapy," Journal of Laser Applications, vol. 5, No. 2-3, pp. 43-60, 1993.

S. Watanabe et al, "Comparative studies of femtosecond to microsecond laser pulses on selective pigmented cell injury in skin," Photochemistry and Photobiology, vol. 53, No. 6, pp. 757-762, 1991.

A.J. Welch et al., "Evaluation of cooling techniques for the protection of the epidermis during HD-yag laser irradiation of the skin," Neodymium-Yag Laser in Medicine and Surgery, Elsevier Science Publishing Co., publisher, pp. 195-204, 1983.

R.B. Yules et al., "The effect of Q-switched ruby laser radiation on dermal tattoo pigment in man," Arch Surg, vol. 95, pp. 179-180, Aug. 1967.

E. Zeitler and M. L. Wolbarsht, "Laser Characteristics that Might be Useful in Biology," Laser Applications in Medicine and Biology, vol. I, M.L. Wolbarsht, editor, Plenum Press, publishers, Chapter 1, pp. 1-18, 1971.

Abstracts Nos. 17-19, Lasers in Surgery and Medicine, ASLMS, Supplement 13, 2001.

Abstracts Nos. 219-223, ASLMS.

Abstracts, various.

Invention description to certificate of authorship, No. 532304, "The way of investigation of radiation time structure of optical quantum generator".

Invention description to certificate of authorship, No. 719439, "The ring resonator of optical quantum generator".

Invention description to certificate of authorship, No. 741747, "The modulator of optical radiation intensity".

Invention description to certificate of authorship, No. SU 1257475 A1, "Laser interferometric device to determine no-linearity of an index of refraction of optical medium".

Invention description to certificate of authorship, No. SU 1326962 A1, "The way of determination of non-linearity of an index of refraction of optical medium".

Request for ExParte Reexamination of U.S. Patent No. 7,274,155, including Exhibits A through E, dated Sep. 4, 2008.

Request for ExParte Reexamination of U.S. Patent No. 6,888,319, including Exhibits A through J, dated Sep. 4, 2008.

Gottlieb, Irving M., "Power Supplies, Switching Regulators, Inverters & Converters" Tab Books Inc., pp. 294-297, © 1984, 1977, 1976.

Wikipedia® Description of Gas Discharge, retrieved from "http://en.wikipedia.org/wiki/Gas-Discharge_lamp", three pages, last modified Aug. 24, 2008.

Wikipedia® Description of Flash Photography, retrieved from "http://en.wikipedia.org/wiki/Flash_(photography)", three pages, last modified Sep. 4, 2008.

FLASHLAMP DRIVE CIRCUIT

CROSS-REFERENCE TO RELATED APPLICATIONS

This application is a continuation of U.S. patent application Ser. No. 11/091,270, filed Mar. 28, 2005 which is a continuation of U.S. patent application Ser. No. 10/600,167, filed Jun. 20, 2003, which is a continuation-in-part of U.S. patent application Ser. No. 10/267,610, filed Oct. 9, 2002, entitled "Flashlamp Drive Circuit" by Mikhail Inochkin, Vycheslav V. Togatov, and Peter O. Gnatyuk, which is a continuation of U.S. patent application Ser. No. 09/797,501, filed Mar. 1, 2001, entitled "Flashlamp Drive Circuit" by Mikhail Inochkin, Vycheslav V. Togatov, and Peter O. Gnatyuk, all of which are incorporated herein by reference in their entirety.

FIELD OF THE INVENTION

This invention relates to pulsed flashlamps and more particularly to improved drive circuits for such flashlamps.

BACKGROUND OF THE INVENTION

Pulsed flashlamps, and in particular Xe filled flashlamps, are used in a variety of applications, including to pump various gas or other laser devices, in various photo, copying, optical detection and optical ranging applications, in cosmetology and in various dermatology and other medical applications. Such lamps normally operate at comparatively high peak voltage, current, and light intensity/power. In order to achieve such high values, power supplies or drives for such lamps typically employ a storage capacitor, which is charged between lamp flashes or pulses, in series with an inductor and some type of switch. Examples of switches used in the past have included thyristors, which once turned on, generally remain on until the capacitor has fully discharged, and transistors. Circuits, such as disclosed in U.S. Pat. No. 4,524,289, which are a modified version of the more standard circuits indicated above, have also been used for driving flashlamps, the primary advantage of such circuits being that they require a smaller capacitor for a given flashlamp having particular voltage and current requirements. U.S. Pat. No. 4,275,335 teaches a flash lamp drive circuit which detects flash lamp current or voltage to control capacitor discharge to maintain substantially constant light intensity.

However, none of the prior art circuits have the capability of producing quickly changing programmable pulse shapes for the flashlamp output, none of these circuits provide protection for circuit components during switch turn-on transitions, something which is generally required for high powered lamp applications, and none of the current circuits are capable of maintaining constant power output from the lamp, and thus constant lamp intensity, when there are fluctuations in lamp impedance, such fluctuations occurring, and sometimes being substantial, as a result of changes in lamp temperature, and as a result of other factors.

Further, with the possible exception of the "335" patent, in none of these circuits is it feasible to produce flashlamp pulses of longer than several milliseconds, the latter problem resulting from the fact that the size of the capacitor utilized increases substantially linearly with pulse width and becomes prohibitively large for most applications beyond a few milliseconds. The size of the required capacitor for a given output is also increased by the relatively low efficiency in capacitor utilization in most of these prior art circuits, such circuits generally utilizing only 20-50% of the energy stored in the capacitor. However, there are applications, particularly medical applications, where the shape of the optical pulses is important in order to achieve a desired therapeutic effect, and in particular to achieve such effect without damage to areas of the patient's body not being treated. For example, in optical dermatology, it may be desirable to rapidly heat a target chromophore to a selected temperature, and to then reduce applied energy so as to maintain the chromophore at the desired temperature. There are also applications where pulses well in excess of a few milliseconds, for example on the order of several hundred milliseconds, may be desirable. The advantages of such long pulses in performing various optical medical procedures, including optical dermatology, is discussed in co-pending application Ser. No. 09/769,960, filed Jan. 25, 2001 and entitled METHOD AND APPARATUS FOR MEDICAL TREATMENT UTILIZING LONG DURATION ELECTROMAGNETIC RADIATION. Flashlamps are one potential source of optical radiation in such applications.

Finally, more efficient utilization of energy stored in the capacitor, which permits the use of smaller capacitors carrying lesser charge, is desirable in all flashlamp applications since it reduces the size, weight and cost of the lamp drive circuitry and enhances the safety of such drive circuits by reducing shock risks. An efficient drive circuit for flashlamps which permits pulses in excess of several milliseconds to be generated without requiring an excessively large capacitor and/or fast, programmable control of pulse shape is therefore desirable.

Another problem with flashlamps is that, in order to avoid premature failure of the lamp, it is desirable that discharge first be established in a low current density simmer mode prior to transfer to an arc mode. This is generally accomplished by triggering to initiate breakdown in the lamp with a triggering circuit, maintaining discharge with a low current DC simmer source and then providing the main current discharge for arc mode from completely separate circuitry. This duplication of components increases the size, weight and cost of flashlamp drive circuits; however, circuitry for permitting sharing of components for at least some of these functions does not currently exist.

SUMMARY OF THE INVENTION

In accordance with the above, this invention provides, for one aspect thereof, a drive circuit for a pulsed flashlamp which includes a capacitor chargeable to a voltage sufficient, when applied across said lamp, to maintain a desired optical output in arc mode, an inductor connected in series with the lamp, a high-speed semiconductor switch connected to, when off, block discharge of the capacitor and to, when on, permit discharge of the capacitor through the inductor and lamp, a one-way path for current flow from the inductor through the lamp at least when the switch is off, a sensor for current through the lamp and a control operative in response to the sensor for controlling the on/off state of the switch to maintain relative power deviation $\alpha = \Delta P/P_o$ through the lamp substantially constant over a desired range of average pulsed lamp powers $P_o$. In the equation, power ripple $$\Delta P = P_{max} - P_{min}, \ P_o = \frac{P_{max} + P_{min}}{2}$$

and $P_{max}$ and $P_{min}$ are maximum and minimum power, respectively, of lamp hysteresis. Thus $\Delta P$ is high when $P_o$ is high and is low when $P_o$ is low. The control may have a reference voltage $V_{ref}$ applied thereto, $V_{ref}$ being a function of the selected $P_o$. The control compares a function of $V_{ref}$ against a voltage function of the sensor output to control the on/off state of the switch. The switch may be turned off when the function of sensor output is greater than a first function of $V_{ref}(V_{ref1})$ and is turned on when the function of sensor output is less than a second function of $V_{ref}(V_{ref2})$, where $V_{ref1} > V_{ref2}$. The control may include a comparator having $V_{ref}$ applied as one input and an output from the sensor applied as a second input, the comparator being configurable to achieve a desired power ripple or hysteresis $\Delta P$. The comparator may include a difference amplifier, $V_{ref}$ being applied to one input of the amplifier through a reconfigurable first voltage divider, and the output from the sensor may be applied to a second input of the amplifier through a second voltage divider. The first voltage divider is normally configured to provide $V_{ref1}$ to the amplifier, and may be reconfigured in response to an output from the amplifier when the switch is off to provide $V_{ref2}$ to the amplifier. Alternatively, the comparitor may include an error amplifier, Vref being applied to one input of the error amplifier and the output from the sensor being applied to a second input of the error amplifier, the output from the error amplifier being applied through a reconfigurable voltage divider to one input of a difference amplifier, and a voltage indicative of lamp current being applied to a second input of the difference amplifier. The voltage divider is normally configured to provide Vref1 to the difference amplifier and is reconfigured when the switch is off to provide Vref2 to the difference amplifier. The lamp normally generates output pulses of a duration $t_p$, with the switch being turned on and off multiple times during each output pulse. The capacitor is normally recharged between output pulses. The control may include a control which selectively varies $V_{ref}$ during each output pulse to achieve a selected output pulse shape. The one-way path may include a diode in a closed loop with the inductor and lamp, the inductor maintaining current flow through the lamp and diode when the switch is off. A mechanism may be provided which inhibits current flow through the diode from the switch during transition periods when the switch is being turned on and the diode is being turned off, this mechanism being a saturable inductor in series with the diode for preferred embodiments, and a saturable inductor may also be provided in series with the switch to inhibit current flow through the switch during such transition periods.

The inductor preferably includes an inductance or load coil wound on a magnetic core which is non-saturating for the operating range of the drive circuit, which core may for example be formed of powdered iron. The coil preferably has a plurality of windings and is also wound on a second core having low losses at high frequency. A primary coil having a number of windings which is a small fraction of the plurality of windings of the inductance coil is wound at least on the second core and a circuit is provided for selectively applying a voltage to the primary coil, the voltage resulting in a stepped up trigger voltage in the inductance coil, which trigger voltage is applied to initiate breakdown in the lamp. The second core is preferably of a linear ferrite material. A DC simmer current source may also be connected to sustain the lamp in a low current glow or simmer mode when the lamp is not in arc mode. Various of the above features, including the features of this paragraph, may be utilized either in conjunction with other features of the invention or independent thereof.

BRIEF DESCRIPTION OF THE DRAWINGS

The foregoing and other objects, features and advantages of the invention will be apparent from the following more particular description of preferred embodiments of the invention as illustrated in the accompanying drawings, the same or related reference numerals being used for like elements in the various drawings.

DETAILED DESCRIPTION

Figure 1:
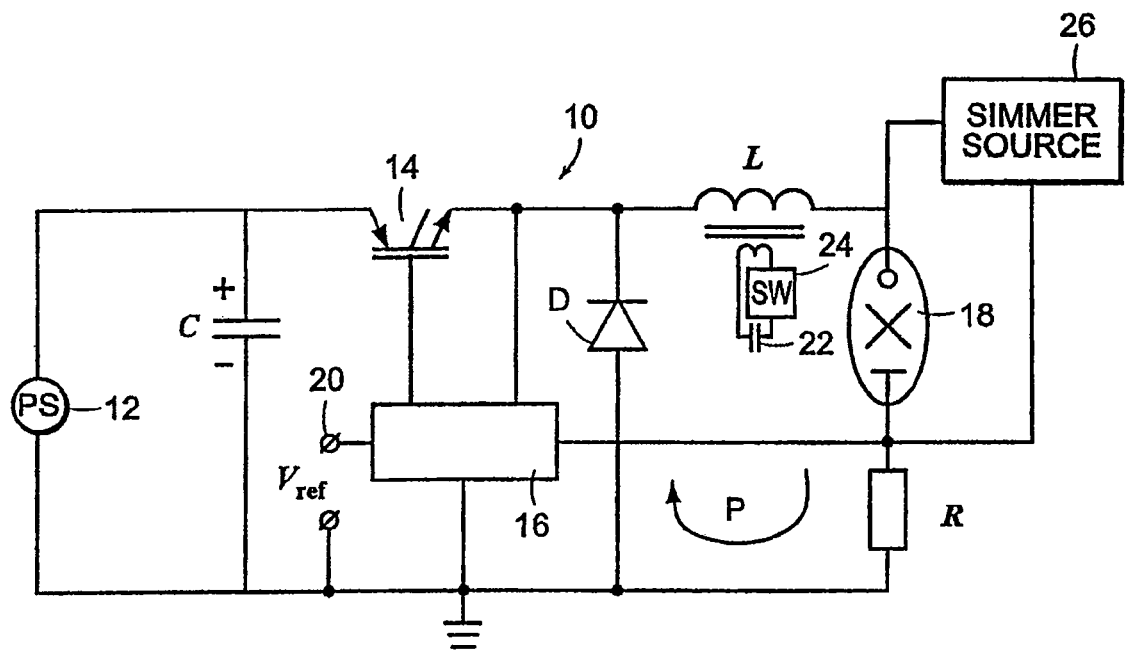
FIG. 1 is a schematic semi-block diagram of a circuit incorporating some of the teachings of this invention.

Referring first to FIG. 1, a pulsed flashlamp drive circuit 10 is shown for an illustrative embodiment of the invention. The circuit includes a capacitor C which is connected to be charged from a suitable power source 12. Power source 12 may be a 120 V, 240 V or other suitable line current, which may be suitably rectified or otherwise processed, may be a battery, or may be some other suitable power source. For illustrative embodiments, charge current from source 12 is only a few amps, for example one to two amps. A standard control circuit (not shown), including a switch, is provided to charge capacitor C to a selected preset voltage E and to prevent overvoltage. Capacitor C discharges through a high speed power switch transistor 14 which is connected to be driven from a control circuit 16, an exemplary such circuit being shown in FIG. 2. The output from switch 14 is applied through an inductor L to one side of pulsed flashlamp 18. The other side of flashlamp 18 is connected through a high speed current sensor to ground. The current sensor may be a resistor R as shown in FIG. 1, may be a Hall effect device, or may be some other suitable current sensor. The junction of flashlamp 18 and the resistor R is connected as a feedback input to control circuit 16 and a reference voltage $V_{ref}$ is applied through terminal 20 as a second input to the control circuit. Where the current sensor is not a resistor, the feedback signal to the control circuit would be obtained from a point in the circuit appropriate for the sensor used. A free wheeling diode D, for example a high power diode with soft recovery, is connected between ground and the input side of inductor L, providing a closed loop path P for current flow from the coil through flashlamp 18, resistor R and diode D. As will be discussed in conjunction with FIG. 3, inductor L may include a multi-turn coil wound on a pair of adjacent cores, one of which functions as the core of a step-up transformer to induce a high voltage trigger pulse or signal for application to lamp 18. The trigger signal comes from a capacitor 22 under control of a switch 24. A simmer current source 26 is also provided to maintain low current glow discharge of lamp 18 when the lamp is not in arc mode. Source 26 is typically a very low current source, typically less than one amp, and as little as a tenth of a amp or less for an illustrative embodiment.

Figure 2:
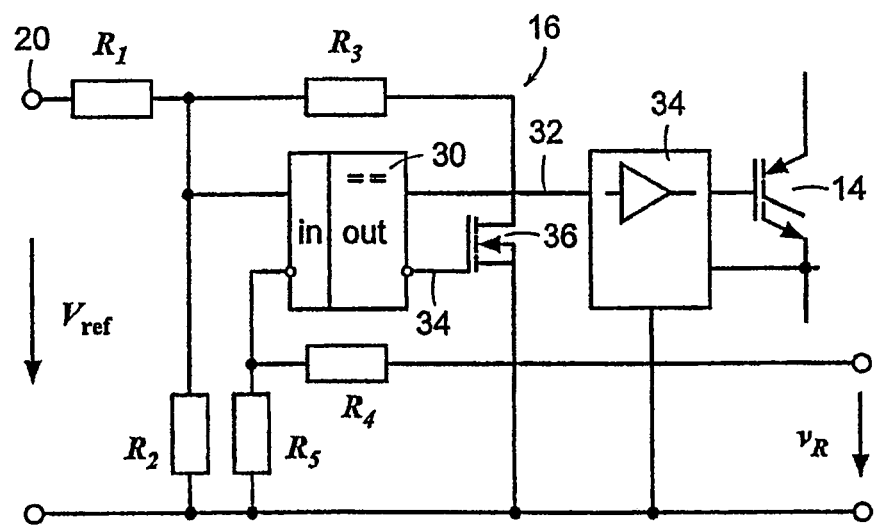
FIG. 2 is a schematic semi-block diagram of a control circuit for use in the circuit of FIG. 1.
Figure 4A:
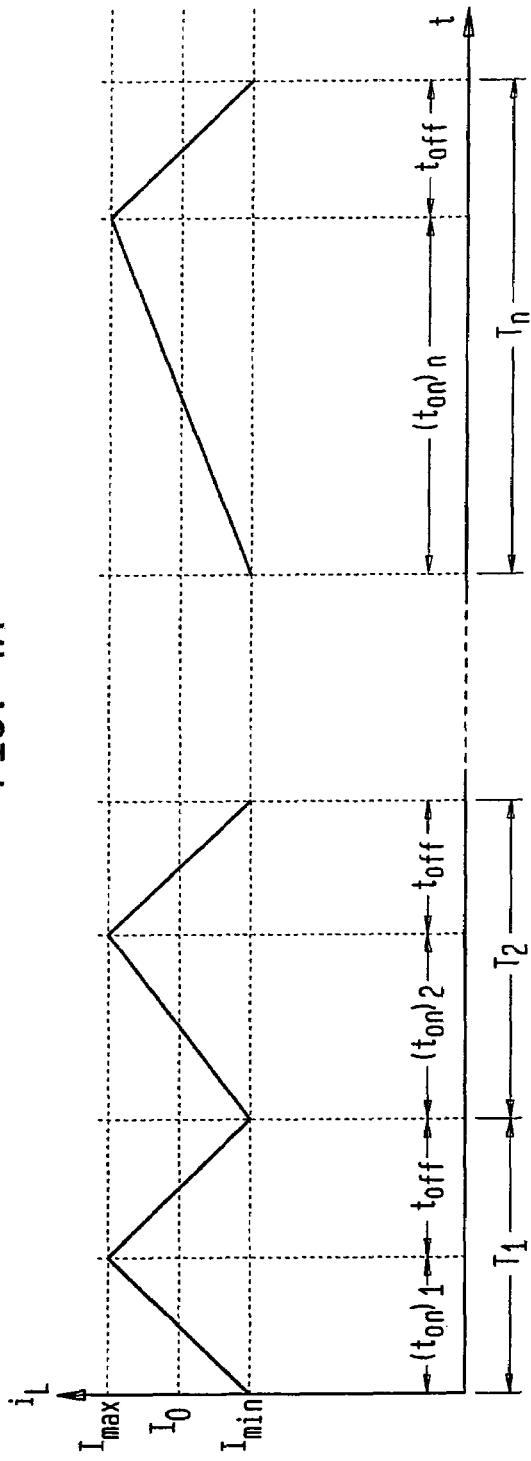
FIGS. 4A and 4B are diagrams illustrating the current/power across the lamp and the voltage across the capacitor respectively during successive on/off cycles of the transistor switch for a single flashlamp pulse.

FIG. 2 shows a control circuit suitable for use as switch control circuit 16. Referring to FIG. 2, it is seen that the reference voltage $V_{ref}$ at terminal 20 is applied through a voltage divider formed by resistors $R_1$ and $R_2$ to one input of a comparison circuit or comparator 30, for example a difference amplifier. The resulting voltage at the input to comparator 30 $V_{ref1}$ is desired maximum value of lamp current $I_{max}$. Current sensor feedback voltage $v_R$ is applied through a voltage divider consisting of resistors $R_4$ and $R_5$ to a second input of comparator 30. When $V_{ref1}$ is greater than $v_R$, comparator 30 generates an output on its direct output 32 which is applied through driver 34 to switch on power transistor 14, permitting capacitor C to discharge through inductor L and lamp 18. However, if $V_{ref1}$ is less than $v_R$, then comparator 30 generates an output only on its inverse output 34 which is applied to turn on transistor 36. The absence of output on direct output 32 causes transistor 14 to switch off. Transistor 36 being on causes resistor $R_3$ to be added to the voltage divider for $V_{ref}$, thereby reducing the voltage applied to the first input of comparator 30 to a $V_{ref2}$ proportional to a minimum current $I_{min}$ which is to flow through lamp 18. $I_{max}$ and $I_{min}$ are shown in FIG. 4A and are discussed in greater detail below.

Figure 3:
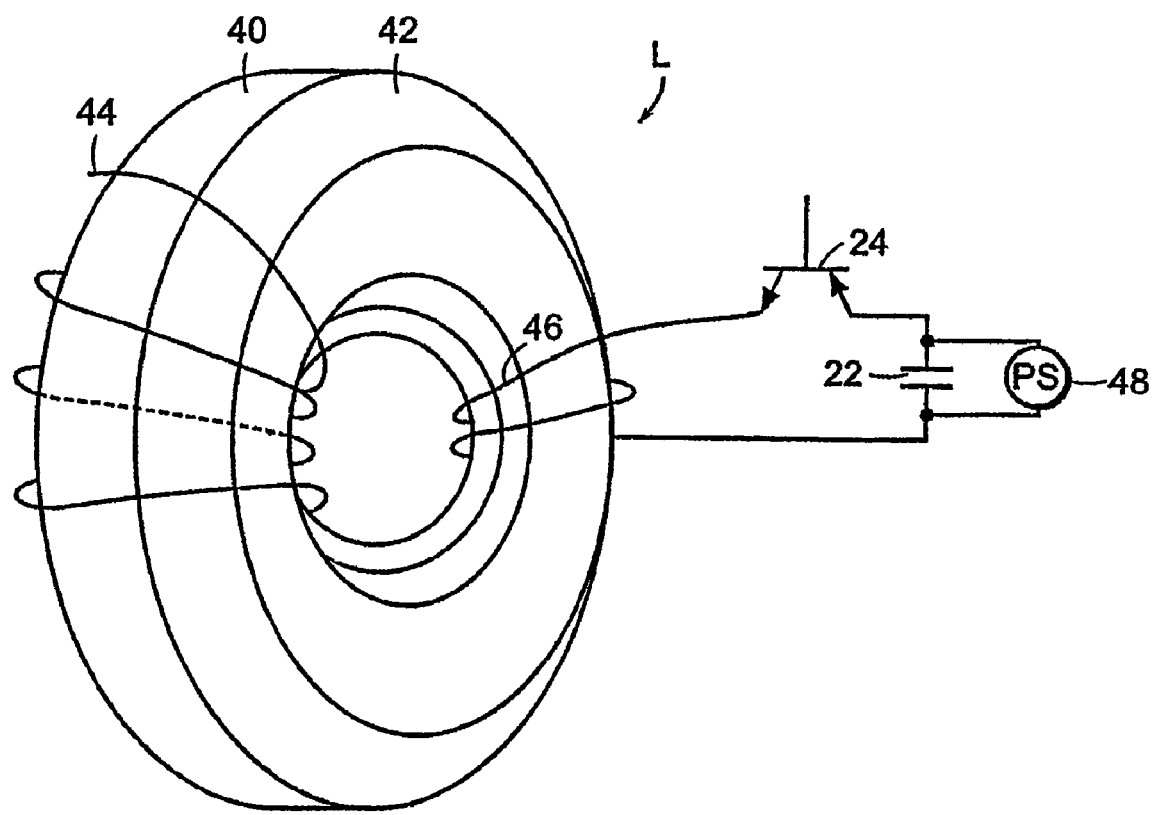
FIG. 3 is a partially schematic perspective view of a coil suitable for use in the circuit FIG. 1.

FIG. 3 is an enlarged diagram of an inductor L for an illustrative embodiment. This inductor being made up of a first core 40, a second core 42, a secondary winding 44 which function as a high voltage source during lamp triggering, and which also functions as an inductance coil or load winding, winding 44 being wound around both cores 40 and 42, and at least one primary winding 46, which is shown as being wound on both cores 40 and 42, but need be wound only on core 42. While only a single primary winding is shown in FIG. 3, this winding may be made up of several windings placed around the circumference of the core to provide proper coupling. As shown in FIG. 1, a triggering signal is applied to primary winding 46 from capacitor 22 under control of switch 24, which switch is preferably a semiconductor switch. The control input to transistor 24 is obtained from a control source which is not shown. Capacitor 22, which is typically relatively small, is charged from a power source 48 which would normally be the same as power source 12, but need not be the same.

For reasons to be discussed shortly, core 40 is of a magnetic material, for example powdered iron, which is non-saturating in the operating range of circuit 10, while core 42 is of a material having low losses at high frequency, for example a linear ferrite. While the cores 40 and 42 preferably have the same inner and outer dimensions, the thicknesses of the cores may be selected so that each is of an appropriate size to perform its desired function, as discussed in the following paragraphs.

Operation

As indicated earlier, in operation, in order to avoid premature failure of lamp 18 as a result of excessive vaporization of electrode material, acoustic shock effects on the lamp walls as the discharge goes directly to high current density arc mode or other causes, it is desirable that breakdown in flashlamp 18 be initially established by a voltage between the lamp electrodes of sufficient amplitude to establish only a weak discharge. This discharge may then be maintained with a low DC simmer current, permitting the much higher amplitude necessary to achieve the desired optical output to then be safely applied to the lamp. In the circuits of FIGS. 1 and 3, this low current density simmer mode discharge is initially established by use of the same coil 44 used for the inductor L in the main discharge or arc mode, thus simplifying and reducing the size, weight and cost of the circuit.

For an illustrative embodiment, coil 44 has approximately 25 windings or turns while primary coil 46 has approximately 2 turns, resulting in an over 10:1 step up ratio. Core 42 is of a size and material having low losses at high frequency, permitting transformation of the low voltage primary signal to the high voltage, fast rise time pulse necessary to break down the gas column in the lamp. The trigger pulse may for example have a duration of one µs. A core material suitable for core 42 is linear ferrite. Since core 42 has a very small volt second capacity, it saturates almost immediately when main voltages/currents are applied to the inductor, and its presence is therefore transparent for the lamp when in arc discharge mode. A voltage induced in winding 46 as a result of current flow through winding 44 is stepped down by for example a factor of 10 to 15 and is therefore not of concern.

Alternatively, the trigger circuit may use two primary windings, each with a dedicated switch, which operate alternately in opposite directions, thereby utilizing the material of core 42 at double its nominal flux capacity, and generating a bipolar trigger signal, further enhancing lamp breakdown.

When trigger switch 24 is activated, current flows in primary winding 46 for a period on the order of 1 microsecond. Core losses in powdered iron core 40 prevent coupling of the two windings by this core; however, the high resistivity and low core losses of ferrite core 42 permit effective coupling and transformation of the several hundred volt primary voltage to a several thousand volts secondary voltage level (for example 8 KV) necessary for lamp ionization. This results in lamp break-down which is then maintained by the DC simmer current from source 26. As indicated earlier, the current from simmer source 26 is generally less than an amp and may be on the order of a tenth of an amp or less.

For the main or arc mode discharge, capacitor C is charged to a value E from power source 12. Control circuit 16 is then enabled, for example by providing an enabling control signal to comparator 30 from an external control, for example a microprocessor, which is not shown. The control may for example operate in response to the detection of simmer current flow through the lamp. Since the current through lamp 18, and thus through resistance R, is initially substantially less than the $I_{max}$ current represented by $V_{ref2}$, comparator 30 generates an output on its direct output line 32 to turn on transistor 14, permitting capacitor C to discharge through inductor L and lamp 18. This causes a rapid increase in the current flow through lamp 18 and initiates the desired arc lamp discharge.

Figure 4B:
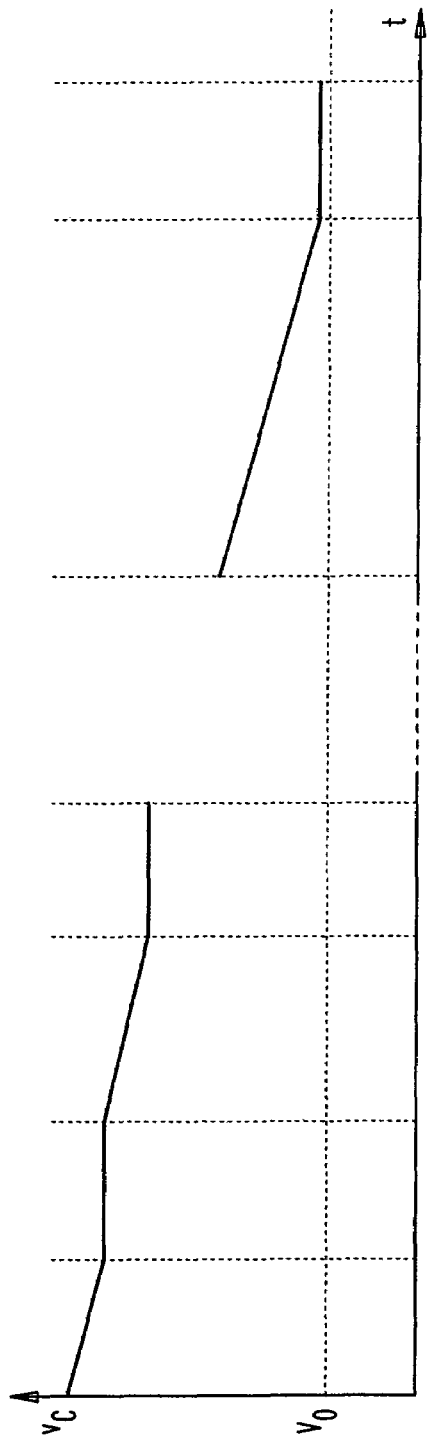

Current continues to increase in lamp 18 until the current is equal to $I_{max}$ (see FIG. 4a) at which time the output on direct output line 32 terminates and comparator 30 generates an output on its inverse output 34. This results in transistor 14 being turned off and transistor 36 being turned on. During the period that transistor 14 was turned on, the signal flowing through inductor L caused energy to be stored in the powdered iron core 40 of inductor L. When transistor 14 is turned off or opened, this energy discharges through path P, and thus through lamp 18 to maintain the desired discharge current therein. As indicated earlier, the turning on of transistor 36 results in a reduced reference voltage $V_{ref2}$ applied to the direct input of comparator 30 which is proportional to $I_{max}$ (FIG. 4a). Thus, transistor 14 remains off and transistor 36 remains on until the current through lamp 18 drops to $I_{min}$, at which time the outputs from comparator 30 again reverse, signal appearing on line 32 to turn on transistor 14 and being removed from line 34, thus turning off transistor 36. As seen in FIGS. 4A and 4B, this results in another drop in the voltage across capacitor C and results in the current across lamp 18 again increasing from $I_{min}$ to $I_{max}$. This cycle repeats until the desired pulse duration $t_p$ is reached, at which time the external control processor for example removes the enabling input from comparator 30. FIG. 4B shows the voltage across capacitor C remaining constant when transistor 14 is off or open, the control for charging of capacitor normally disabling charging during the arc mode discharge to prevent potential EMI between charge and discharge circuits. While this is not a limitation on the invention, charging the capacitor when in arc mode is of little consequence since the charging current is only on the order of one to two amps, while $I_o$, the average discharge current through the lamp may be up to 250 amps or more. FIG. 4A also shows the on time of transistor 14 increasing for successive cycles. This follows from the drop in voltage across the capacitor (see FIG. 4B) for each cycle of switch 14.

Each complete cycle of control circuit 16 lasts on the order of 25 microseconds for an illustrative embodiment, a time far beyond the volt-second interval capability of the linear ferrite used for core 42. The switching of transistor 14 thus occurs at tens to hundreds of kilohertz. Therefore, since the pulse durations $t_p$ contemplated for lamp 18 are generally in the millisecond range, and may, utilizing the teachings of this invention, be as long as 200 milliseconds or more without requiring an excessively large capacitor C, there can be hundreds of cycles of transistor switch 14 for each lamp pulse. In accordance with the teachings of this invention, this permits the shape of the pulse to be controlled by modifying $V_{ref}$, either upward or downward, in order to increase or decrease lamp output during the course of a pulse, and thus to vary pulse shape. A processor, for example a microprocessor (not shown), may be programmed to control the $V_{ref}$ applied to terminal 20 for each cycle of transistor 14 in order to achieve a desired pulse shape for lamp 18. $V_{ref}$ may also be controlled to achieve a desired color temperature for the lamp (i.e. to control the temperature of the lamp so as to maximize/minimize selected wavelengths in the lamp output). However, because of the voltage dividers used in setting the inputs to comparator 30, the relative current deviation $\alpha = \Delta I/I_o = I_{max} - I_{min}/0.5(I_{max}+I_{max})$ remains substantially constant, regardless of $V_{ref}$, and thus of the average current $I_o$ through the lamp. The values of the resistors R1-R5 can be selected in a manner to be described later to achieve the desired substantially constant $\alpha$.

Operating with a substantially constant $\alpha$ has a number of advantages. First, the mathematical condition providing the substantially constant relative current deviation is $$E^2 - V_0^2 \rangle \frac{2P_0}{C} t_p \qquad (1)$$

where E is a voltage across capacitor C, $V_0$ is a voltage on the lamp, $P_0 = I_0 V_0$, $I_0$ is the average current on the lamp and $t_p$ is the duration of the flashlamp pulse. Since the mean current value $I_0$ does not depend on the initial voltage E on the capacitor and is set by the control circuit ($I_0=0.5(I_{max}+I_{min})$), E may be set as high as 3-4 times the voltage on the lamp. Since energy utilization is a function of $(E^2-V^2/E^2)$ where V is the lamp voltage, this permits the maximum energy which can be delivered to the lamp during a pulse without power decrease to be approximately 90% of the energy stored in the capacitor [(i.e. $(E^2-V^2)/E^2$ becomes $(3^2-1^2/3^2=8/9$ or $(4^2-1^2)/4^2=15/16$], this being substantially greater than the 20-50% energy utilization of the capacitor in prior art circuits. The more efficient utilization of capacitor energy permits greater lamp input/output for a given capacitor or the use of a smaller, less expensive capacitor for a given lamp output.

Further, while for prior circuits, the required value of the capacitor increases substantially linearly with increases in pulse duration, and normally becomes prohibitively large for pulses in excess of a few milliseconds, the circuit of this invention permits output pulses of up to several hundred milliseconds to be achieved without requiring any increase in capacitor value. In particular, for the circuit of FIG. 1, operating with $\Delta I/I_0$ being substantially constant, the capacitance C is given by $$C = \frac{2W}{E^2 - \left(\frac{Wk_0^2}{t_p}\right)^{\frac{2}{3}}} \qquad (2)$$

where W is the total energy for the pulse of duration tp, and $k_0$ is the characteristic lamp impedance which is defined by the length "l" and the diameter "d" of the lamp discharge space ($k_0=1.28l/d$).

Thus, the capacitor C is substantially independent of pulse width or duration $t_p$ and, in fact, decreases slightly for increased $t_p$. By contrast, for most prior art circuits, the value of C increases linearly as a function $t_p$.

Still, another advantage of operating with a substantially constant $\Delta I/I_0$ is that the value of the inductance "L" is inverse to the value of current deviation $\Delta I$. Thus, by maintaining the substantially constant relative current deviation $\alpha$, the inductance value may be minimized, being substantially less than in some prior art circuits.

In order to achieve the substantially constant relative current deviation $\alpha$ discussed above, the following relationship for the resistor R1-R5 of FIG. 2 are required.

$$\frac{R_5}{R_4} < \frac{2}{\alpha} \qquad (3a)$$

$$\frac{R_2}{R_1} = \frac{(R_5/R_4) \cdot (2+\alpha)}{2-(R_5/R_4) \cdot \alpha} \qquad (3b)$$

$$R_3 = \frac{R_2}{1+(R_2/R_1)} \cdot \left(\frac{1}{\alpha} - \frac{1}{2}\right) \qquad (3c)$$

The above equations assume that the voltage $V_0$ corresponding to the mean value of lamp current $I_0$ is equal to $V_{ref}$, this condition simplifying resistor network balancing. If $R_5=R_4$, then the calculation of resistors for a given ratio of relative current deviation $\alpha$ may be simplified to $$\frac{R_2}{R_1} = \frac{2+\alpha}{2-\alpha} \qquad (4a)$$

$$R_3 = \frac{R_2 \cdot (2-\alpha)^2}{8 \cdot \alpha} \qquad (4b)$$

While the circuits described above can provide the indicated advantages so long as the lamp impedance Ko remains substantially constant, since illumination intensity is a function of average pulsed lamp power, where Ko varies during a light pulse, or between pulses, undesired variations in lamp intensity can also occur where lamp operation is controlled only in response to lamp current or lamp voltage. It has been found that this problem, caused by variations in lamp temperature or other causes, can result in variations of 10% to 20% or more between successive lamp pulses. These problems are overcome by the circuits of FIGS. 5-7. While to simplify these drawings, components such as power source 12, simmer source 26 and the components of FIG. 3 are not shown in these figures, these components could, if desired, be used with the embodiments of these figures for the same reasons and in the same way as for the prior embodiments.

Referring to FIG. 5, it is seen that, in additional to the missing parts discussed above, FIG. 5 also differs from FIG. 1 in that it includes a saturable inductor 50 between switch 14 and inductor coil L, a saturable inductor 51 in series with diode 5, a pair of series connected resistors 57a and 57b between the output side of inductor L and ground, and a high speed multiplier 59 having a voltage Vi indicative of lamp current as one input and a voltage Vv indicative of lamp voltage as its other input, the voltage Vv being taken at the junction of resistors 57a and 57b. While the voltage Vv is not equal to the lamp voltage, it is proportional to the lamp voltage, and any differences can thus be compensated for in multiplier 59, by other components of the circuit or in the selection of Vref. The output Vp from multiplier 59 is thus indicative of lamp power and is applied as the feedback input to switch control circuit 56.

Figure 5:
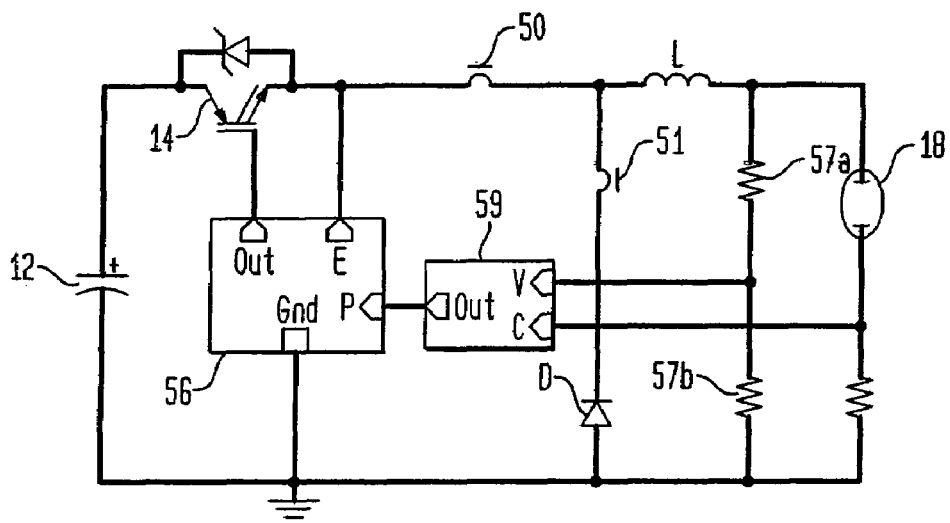
FIG. 5 is a schematic semi-block diagram of an alternative preferred circuit for practicing the teachings of the invention.

Saturable inductors 50 and 51 are provided in the circuit of FIG. 5 to protect switch 14 and diode D respectively, as well as other circuit components from current overload during each switch turn on/diode turn off transition. In particular, during the period the switch is turning on, which may be from tens to hundreds of nanoseconds, diode D is still fully saturated with charge carriers as a result of the direct current flow therethrough from inductor L through path P. The recovery or closing time for the diode can be several tens of nanoseconds for the fastest diodes. This results in a low resistance spurious path for current flow through the switch and in the reverse direction through the diode. This current flow, which can easily reach several hundred amps, can damage the switch, the diode and other components in this spurious current flow path. Inductors 50 and 51 provide a high impedance to the spurious currents during the transition period until diode D recovers and then saturate so as to disappear from the circuit during normal flow of current from switch 14 through inductor L and lamp 18.

Figure 6:
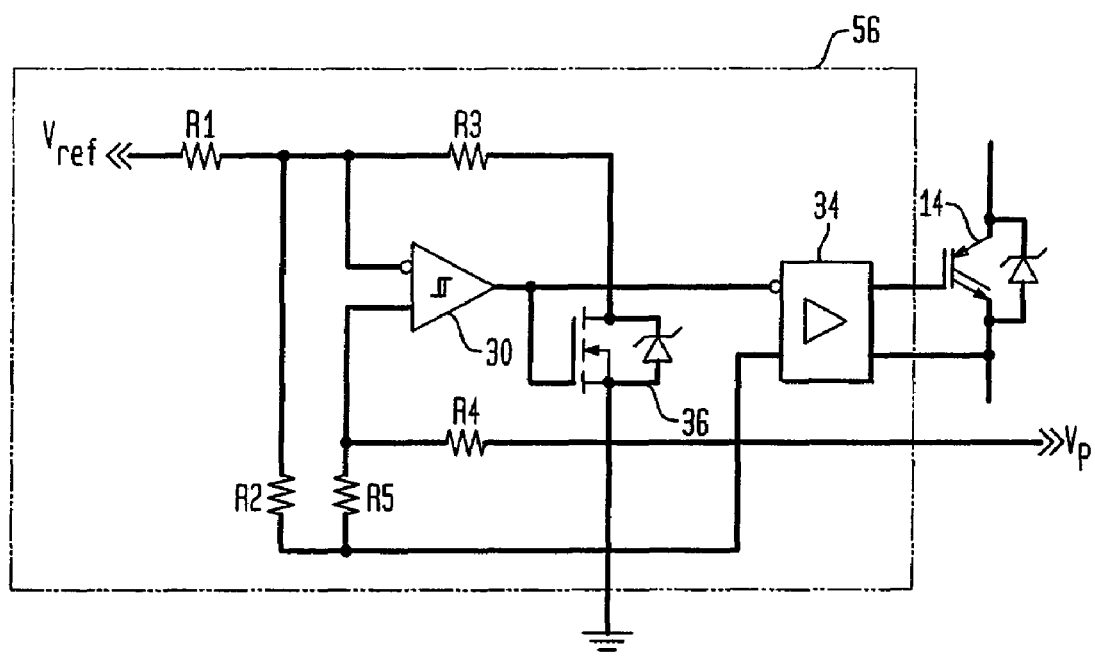
FIG. 6 is a schematic semi-block diagram of a control circuit for use in the circuit of FIG. 5.

FIG. 6 illustrates one embodiment of a control circuit 56 suitable for use in the circuit of FIG. 5, which circuit is the same as that of FIG. 2, and operates in substantially the same way as the circuit of FIG. 2, except that the input to the difference amplifier through resistor R4 is indicative of lamp power rather then lamp current and Vref is selected to achieve a desired average pulsed lamp power rather then a desired average lamp current. Switch 36 still functions in the same way to provide the desired Pmax/Pmin hysterisis. However, since control of the lamp is based on detected pulsed lamp power rather then lamp current, illumination can be maintained substantially constant regardless of variations in lamp impedance.

Figure 7:
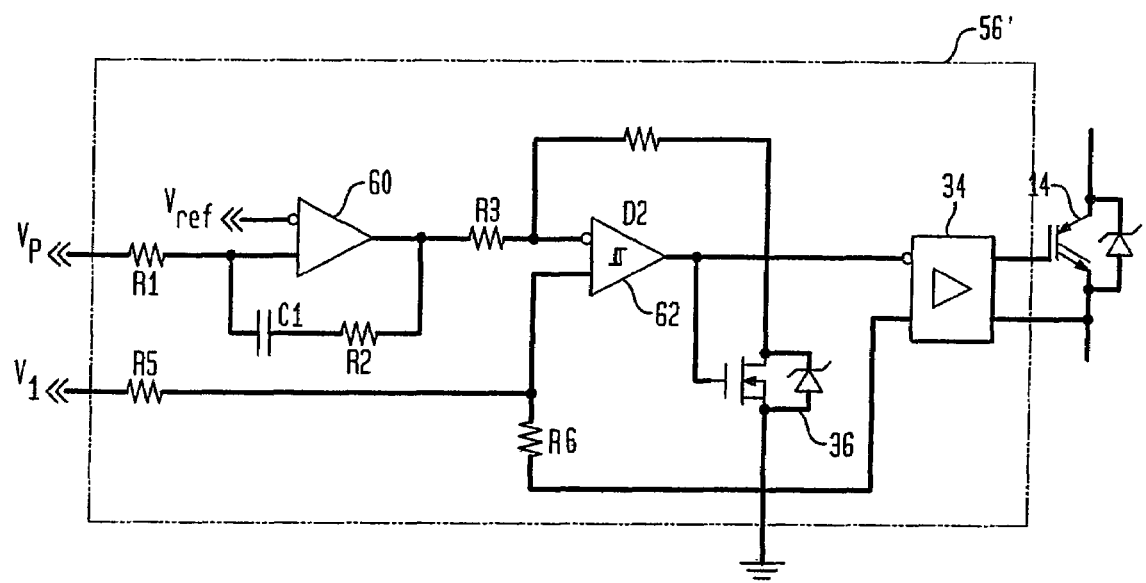
FIG. 7 is a schematic semi-block diagram of an alternative control circuit for use in the circuit of FIG. 5.

FIG. 7 illustrates an alternative control circuit 56' which may be advantageous in some applications. In this circuit, an error amplifier 60 is provided to which the Vp and Vref inputs are applied. The amplified power error output from error amplifier 60 is applied as one input to difference amplifier 62, the other input to this amplifier being a voltage indicative of lamp current. Switch 36 varies the error signal applied to amplifier 62 in the same way this component varies reference signals for prior embodiments to achieve the desired hysterisis. The remainder of the circuit functions the same as for prior embodiments.

The circuit of FIG. 7 may reduce the speed requirements for multiplier 59, permitting a significantly less expensive multiplier to be utilized. This results from the error amplifier strongly integrating power ripple in the Vp input signal. The circuit of FIG. 7 also greatly decreases high frequency noise caused by switching of power components in the circuit. This increases stabilizing properties of the circuit on the pulse "shelves", but can distort the edges of the pulses. Therefore, the circuit of FIG. 7 is preferable for applications where long pulses with high stability of peak power are required, such applications including, for example, certain medical applications, while the circuit of FIG. 6 may be preferable for applications having short pulses and good dynamic properties for programmable pulse shape.

While the comparator 30,62 is assumed to have a fixed hysteresis, so that an external reconfigurable voltage divider is required to vary the hysteresis, this is not a limitation on the invention and, if available, a comparator having a controlled or controllable variable hysteresis could be used, eliminating the need for the external voltage dividers. In addition, while the invention has been described above with reference to preferred embodiments, and various modification thereof have also been discussed, it is to be understood that these embodiments and the variations discussed are for purposes of illustration only and that the foregoing and other changes in form and detail may be made therein by one skilled in the art while still remaining within the spirit and scope of the invention which is to be defined only by the appended claims.

What is claimed is:

1. A circuit for activating a lamp, comprising
an inductor comprising a primary winding and a secondary winding wound on a pair of adjacent cores, one of said cores exhibiting low losses at high frequency and the other being non-saturating during steady state operation of said lamp, said secondary winding being coupled in series with said lamp,
a capacitor coupled across said primary winding,
a trigger switch coupled to said capacitor, wherein activation of said switch causes flow of a current from the capacitor to the primary winding so as to induce a voltage across the secondary winding sufficient to establish a weak discharge in the lamp, and
a source for providing a DC simmer current to the lamp so as to maintain said weak discharge.

2. The circuit of claim 1, wherein said weak discharge is characterized by a current of less than about 1 amp flowing through the lamp.

3. The circuit of claim 1, wherein the current flow from the capacitive device to said primary winding has duration of about one microsecond.

4. The circuit of claim 1, wherein said core exhibiting low losses at high frequency comprises linear ferrite.

5. The circuit of claim 1, wherein said non-saturating core comprises powdered iron.

6. The circuit of claim 1, wherein a ratio of a number of turns of the secondary winding to the primary winding is 10:1.

7. The circuit of claim 1, further comprising:

another capacitor coupled in series with said lamp, a semiconductor switch coupled in series between said another capacitor and said lamp, and a control circuit for enabling said semiconductor switch in response to detection of a simmer current to cause discharge of energy stored in said another capacitor into the lamp so as to cause operation of the lamp in an arc mode.

8. The circuit of claim 7, wherein said control circuit comprises a comparator applying an enable/disable signal to said semiconductor switch.

* * * * *